United States Patent [19]
Paulos

[11] Patent Number: 5,271,403
[45] Date of Patent: Dec. 21, 1993

[54] ULTRASOUND IMAGING SYSTEM
[76] Inventor: John J. Paulos, 10809 Bexhill Dr., Raleigh, N.C. 27606
[21] Appl. No.: 755,435
[22] Filed: Sep. 5, 1991
[51] Int. Cl.$^5$ ............................................. A61B 8/00
[52] U.S. Cl. ............................................. 128/660.07
[58] Field of Search .................. 128/660.01, 660.07, 128/661.01, 661.07-661.10, 713, 902-904

[56] References Cited
U.S. PATENT DOCUMENTS

| | | | |
|---|---|---|---|
| 4,534,221 | 8/1985 | Fife et al. ................... | 128/661.01 X |
| 4,817,066 | 3/1989 | Takasugi et al. ........... | 128/660.01 X |
| 4,819,652 | 4/1989 | Micco .......................... | 128/661.09 |
| 4,917,097 | 4/1990 | Proudian et al. ........... | 128/661.01 X |

Primary Examiner—Francis Jaworski
Attorney, Agent, or Firm—Ratner & Prestia

[57] ABSTRACT

The present invention relates to a medical ultrasound imaging system having a remote transducer located on a handle unit which is connected to a system box or unit through a coaxial cable. Transmission pulses are sent from the system box to the transducer through the coaxial cable to produce sound waves which are directed into a patient's body. These sound waves are reflected from internal organs back to the transducer and converted into electrical input signals. A split-cascode preamplifier having a MOSFET driver located on the handle unit and a cascode device and resistive load located in the system box is used for preamplifying the input signals created at the remote transducer. The MOSFET driver is biased by a MOSFET switch to help eliminate noise created by the use of ordinary resistive biasing means. A diode coupling network is used to transmit pulses from the system box to the transducer while decoupling the cable capacitance from the preamplifier input. A protective diode is placed in series with the MOSFET driver to protect the driver from the transmit pulse. This diode and the coupling network enable the handle unit and system box to be coupled by a single coaxial cable. Other applications that require a remote sensor to produce input signals and amplification of the input signals prior to transmission to a separate unit may also be improved by the present invention.

20 Claims, 4 Drawing Sheets

1

ULTRASOUND IMAGING SYSTEM

FIELD OF THE INVENTION

The present invention relates generally to an ultrasound imaging system and more particularly to a preamplifier for an ultrasound imaging system having a relatively high gain and wide bandwidth.

BACKGROUND OF THE INVENTION

Medical ultrasound imaging is a widely used and cost effective diagnostic tool in internal medicine. In essence, ultrasound imaging systems use sound waves to create an image of a patient's internal tissues and organs. A physician can the use this image as a diagnostic tool in treating the patient. Structurally, an ultrasound imaging system typically includes a hand-held handle unit, a main system unit physically separated from the handle unit, and coaxial cables connecting the handle unit to the main system unit. The handle unit contains a transducer or transducer array and may include preamplifiers. The system unit contains additional processing circuits to produce the ultrasound images.

To operate the imaging system, a medical operator places the handle unit at a selected position adjacent to a patient's body. The operator turns on the imaging device and electrical transmission pulses are sent to the transducer. The transducer converts these electrical transmission pulses into sound waves which are directed into the patient's body. These sound waves penetrate the patient's body and components of the sound waves are reflected back toward the handle unit and impact the transducer. The transducer converts the acoustical energy from the reflected sound waves into electrical input signals representing the reflected sound waves. These input signals are transferred from the handle unit through the coaxial cable to the system box where the input signals are processed to produce diagnostic output readings. The input signals may be preamplified in the handle unit prior to transmission across the coaxial cables, but most current systems do not include preamplifiers in the handle unit.

For the typical medical ultrasound system, the transducer in the handle unit includes arrays of piezoelectric transducers. Ultrasound imaging systems produce improved images if the system is operated at high frequencies, but to produce these high frequencies large numbers of small element are necessary. Use of large numbers of small elements at the remote sensor creates a high effective source impedance which causes much of the input signal to be lost when the input signal is transmitted across high capacitance coaxial cables.

This problem of high source impedance and input signal loss during transmission across the coaxial cables is sometimes handled by the prior art by placing a preamplification stage in the handle unit. The preamplification stage typically uses JFET or MOSFET devices in a common source architecture. Resistive biasing means are used to bias the transistors used in the handle unit preamplifiers. One problem with this method of preamplification is that the preamplifier load resistor must be small to attain an acceptable bandwidth for the preamplifier. The small load resistor, however, reduces the preamplifier gain and causes greater noise. Another problem is that the resistive biasing of the preamplifier transistors creates additional noise in the handle unit preamplifier. Placing a complete preamplifier in the handle also leads to heat dissipation problems and possible bulkiness of the handle unit.

In some ultrasound system applications, the transducer signals are multiplexed. Multiplexing involves a system design that permits the system unit to select only a portion of the transducers to be read out and processed for each transmission pulse. When using a multiplexing system, switching must be provided in the handle to allow for selective operation of only a portion of the transducers.

SUMMARY AND OBJECTS OF THE INVENTION

The present invention is a medical ultrasound imaging device that overcomes disadvantages of prior art medical imaging devices. The improved imaging device includes three main structural units: a handle unit, a main system unit physically separated from the handle unit, and an interconnecting electrical coupler for connecting the handle unit to the system unit. Within the handle unit is a transducer which converts transmission pulses generated at the system box into sound waves that are directed into a patient's body. Reflected sound waves are then echoed back towards the handle unit and the transducer converts the acoustical energy of the reflected sound waves into electrical input signals.

These input signals must be buffered or amplified prior to transmission from the handle unit to the main system unit where the input signals are processed to produce an ultrasound image. A split-cascode preamplifier is used to preserve or amplify the input signal level during transmission to the system unit, while avoiding many of the problems associated with prior art devices. The split-cascode preamplifier includes a drive section in the handle unit and a load section in the system unit box. More particularly, a MOSFET transistor driver having a common source architecture is placed in the handle unit, and a cascode transistor and resistive load are located in the system box. The transistor driver modulates the current flowing through the coaxial cable, and this current modulation is transferred to the resistive load by the cascode device (a bipolar junction transistor in common base configuration).

The input signal produced by the transducer is coupled to the preamplifier and transmitted to the gate of the transistor driver by a coupling capacitor. The coupling capacitor and additional protective diodes help protect the transistor driver from the transmission pulse. A MOSFET switch provides biasing for the transistor driver. The MOSFET switch is momentarily closed after the transmit pulse reaches the transducer and before the arrival at the MOSFET driver of the acoustical signals of interest. The MOSFET switch provides a biasing DC potential at the MOSFET driver gate which is stable for an adequate time to amplify the input signal. The use of a switched biasing element eliminates the large noise component associated with the use of resistive biasing.

To enable a single coaxial cable to transmit both transmission pulses and input signals, the present invention uses a diode coupling network to transmit the transmission pulses to the transducer and an external protective diode in series with the transistor driver's output. The external protective diode is reversed biased during transmission of a transmit pulse and thus protects the transistor driver. The diode coupling network permits the transmission pulses to pass through to the transducer, but is effectively an open circuit to the small electrical input signals produced by the transducer.

The present invention ultrasound system also allows applications where the transducer's signals are multiplexed to reduce the cable count. For this type of system application, a MOSFET switch is placed in series with each transistor driver's open drain output. The MOSFET switches can then be turned on or off to selectively choose which transistor driver's output will be transmitted to the system box. The use of MOSFET switches to realize output multiplexing enables the multiplexing circuit to be placed on the same integrated circuit containing the transistor drivers and also results in no power dissipation in the unselected transistor drivers.

It is therefore an object of the present invention to provide a medical ultrasound system having a split-cascode preamplifier with the driver located in the handle unit and the cascode device and resistive load located in the system box in order to provide improved preamplifier gain and bandwidth performance and lower power dissipation.

Still a further object of the present invention resides in the use of a switched biasing means for the driver transistor in order to eliminate unnecessary noise in the preamplifier.

Still a further object of the present invention resides in the use of a diode coupling network which permits a single coaxial cable to couple the handle unit to the system box.

Another object of the present invention is to minimize the size of the preamplifier stage in the handle unit by placing the driver transistor, biasing means, protection diodes, and coupling capacitor all on one integrated circuit.

Still another object of the present invention is the use of series MOSFET switches to realize output multiplexing on the same integrated circuit as the transistor drivers and with no power dissipation in the unselected channels.

Other objects and advantages of the present invention will become apparent and obvious from a study of the following description and the accompanying drawings which are merely illustrative of such invention.

DETAILED DESCRIPTION OF THE INVENTION

Figure 1:
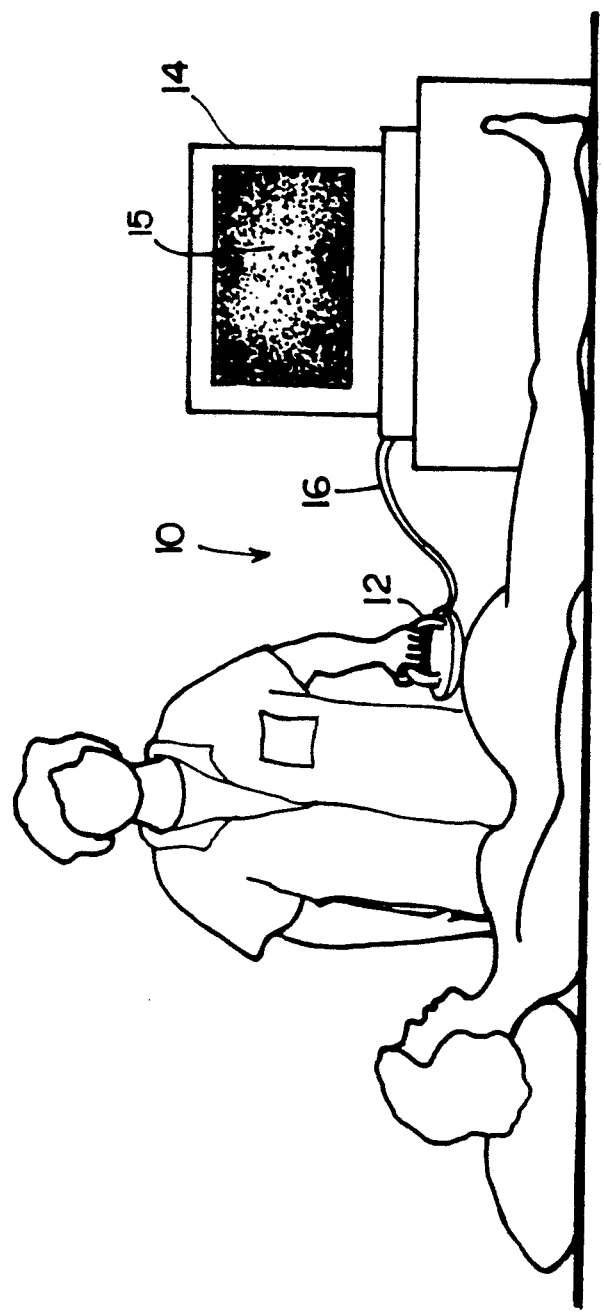
FIG. 1 is an elevation view of the ultrasound imaging system incorporating the split-cascode architecture of the present invention.
Figure 2:
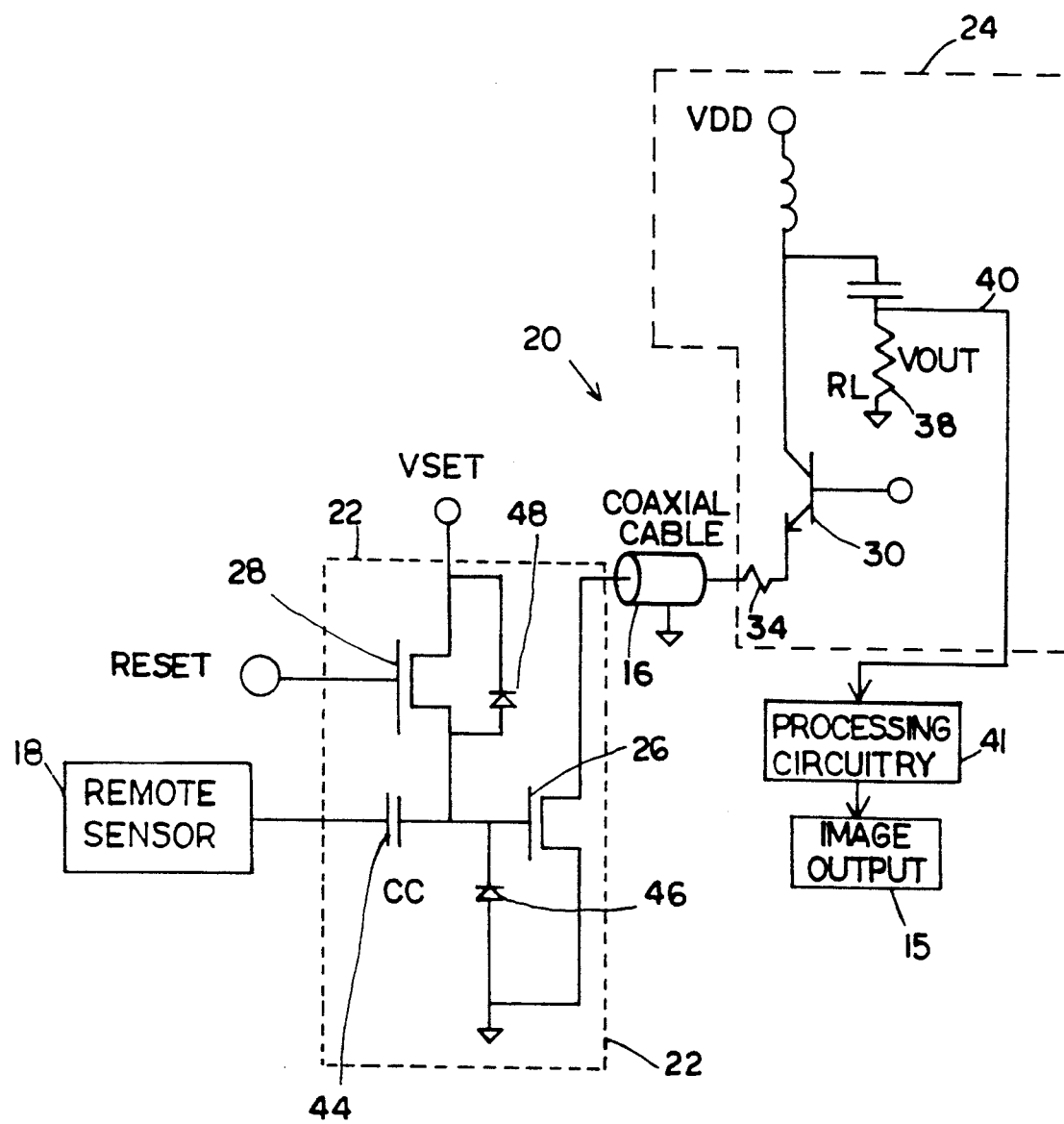
FIG. 2 is a schematic diagram of the split-cascode preamplifier.
Figure 3:
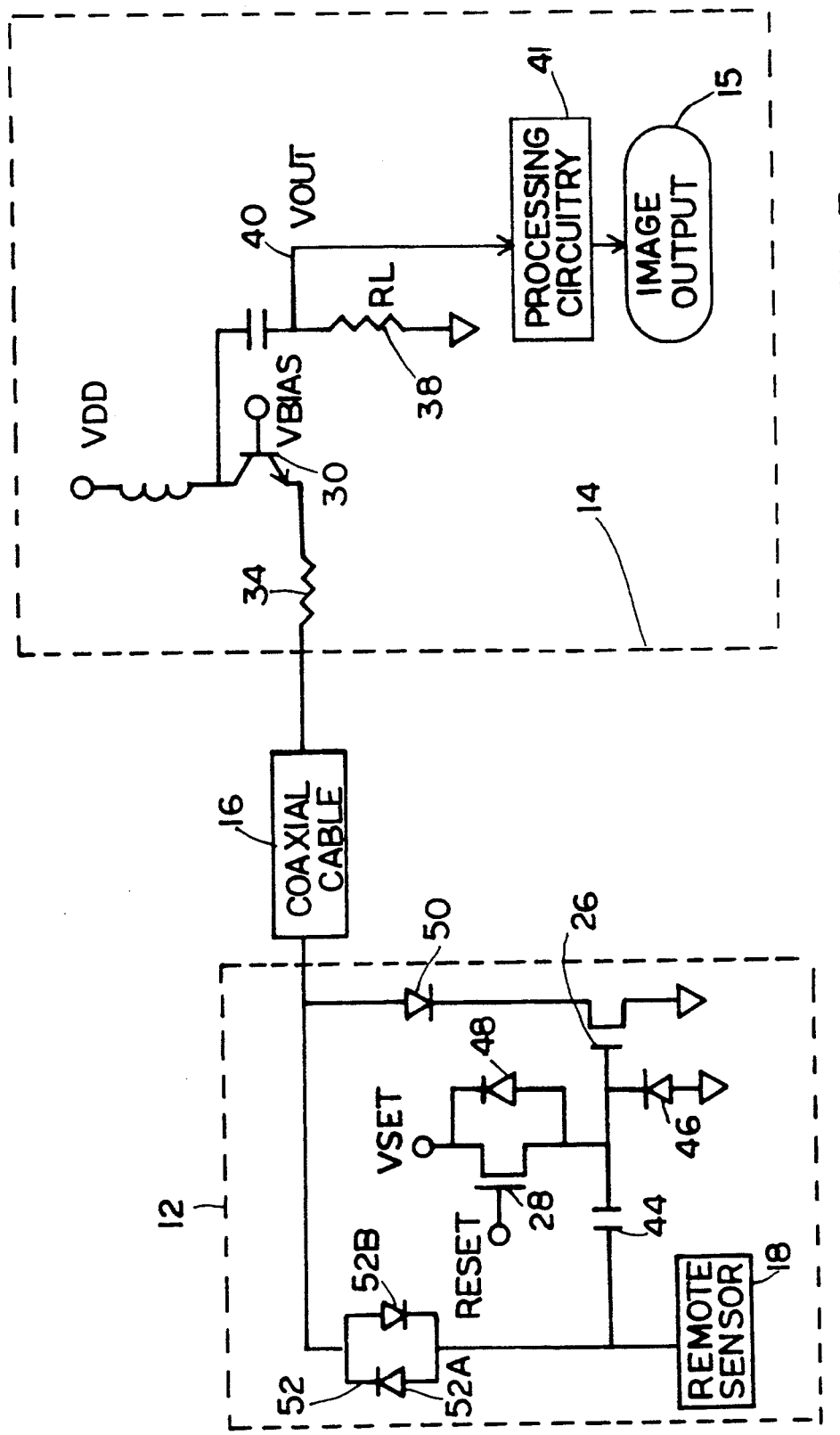
FIG. 3 is a schematic diagram illustrating the split-cascode preamplifier and additional circuitry enabling a single coaxial cable to couple the handle unit to the main system unit.
Figure 4:
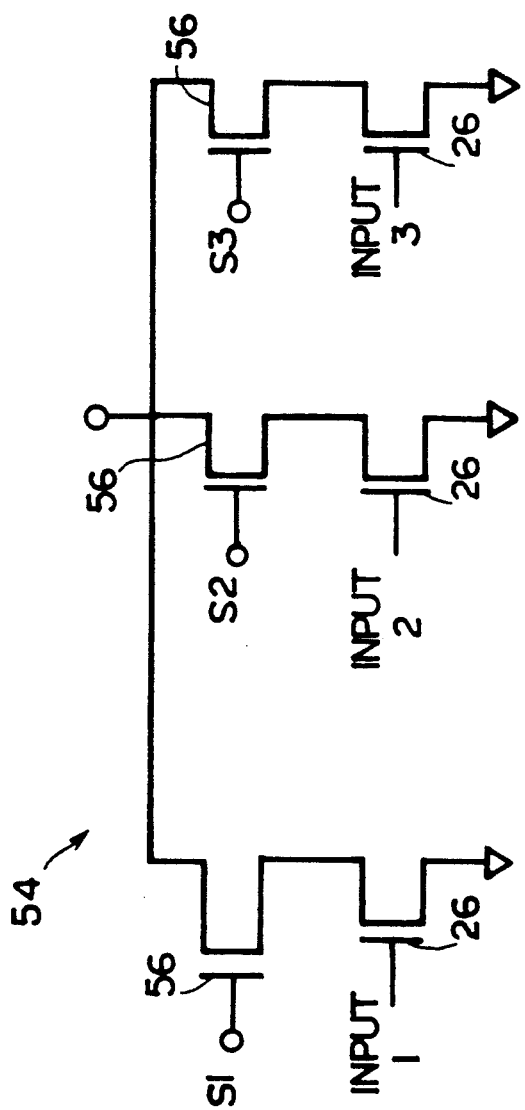
FIG. 4 is a schematic illustration of multiplexing circuitry used in the present invention.

Referring now to the drawings, the medical ultrasound imaging system of the present invention is shown therein and indicated generally by the numeral 10. As shown in FIG. 1, the imaging system's main structural components include a handle unit 12, a main system box 14 structurally separated from handle unit 12, and an electrical coupler 16 coupling handle unit 12 to system box 14. Located within the handle unit 12 and system box 16 are electrical components which help create ultrasound images. FIGS. 2, 3, and 4 schematically illustrate electrical components used in the imaging system 10, and also indicate the positioning of electrical components between the handle unit 12 and system box 14. The choice of position of particular electrical components in either the handle unit 12 or main system box 14 is important to the operation of system 10, as will be described.

As illustrated in FIG. 2, imaging system 10 includes a transducer 18 located in the handle unit 12. Transducer 18 is a conventional piezoelectric transducer and converts electrical transmission pulses into sound waves that are directed into a patient's body. These sound waves are reflected from internal organs back toward handle unit 12 and impact transducer 18. Transducer 18 converts these reflected sound waves into electrical input signals. The input signals are transmitted from handle unit 12 through coaxial cable 16 to system box 14 where the input signals are processed to produce diagnostic images. Due to the high source impedance of transducer 18 and high capacitance of the coaxial cable 16, amplification of the input signals prior to transmission across coaxial cable 16 is desired.

Imaging system 10 uses a split-cascode preamplifier 20 to amplify the input signals created by remote sensor 18. The split-cascode preamplifier 20 is divided into a drive section 22 located in the handle unit 12 and a load section 24 located in the system box 14. Drive section 22 includes a MOSFET driver 26, a MOSFET biasing switch 28, a coupling capacitor 44, and protection diodes 46 and 48. By using CMOS technology, the driver section 22 can all be placed on one integrated circuit. The input signal from the transducer 18 is transmitted to the transistor driver 26 which modulates the current flow through the load section.

MOSFET switch 28 provides a switched DC bias at the gate of the MOSFET driver 26. A properly timed reset signal at the gate of MOSFET switch 28 places switch 28 in an "on" state prior to an input signal reaching the gate of transistor driver 26. The "on" time of the switch 28 can be less than one-hundred nanoseconds and the DC potential at the gate of transistor driver 26 will be stable for several tens of milliseconds due to the low leakage of the switch 28. Proper timing of switch 28 and the low leakage of switch 28 results in a stable DC bias for driver 26.

Coupling capacitor 44 and protection diodes 46 and 48 are located at the preamplifier input to protect the preamplifier input from transmission pulses. Coupling capacitor 44 will stand off the large DC voltage of the transmission pulse and also limits the pulse's transient current which will be absorbed by protection diodes 46 and 48. Use of a coupling capacitor 44 to transmit input signals to MOSFET driver 26 enables switched biasing to be used for driver 26.

The preamplifier's load section 24 includes a cascode transistor 30, a matching resistor 34, and a load resistor 38. The modulated current provided by the transistor driver 26 is transmitted through coaxial cable 16, the cascode transistor's emitter, and passed to the preamplifier's load resistor 34. In the preferred embodiment, the cascode device 30 is a common base transistor, but a common gate transistor could also be used. The split-cascode architecture results in an extremely low driving point resistance at the emitter of the common base transistor 30. Accordingly, the capacitance at the emitter node due to the coaxial cable 16 has little impact on the bandwidth of the preamplifier stage. Load resistor 38 can be freely selected for high gain without substantially affecting bandwidth because it is faced with a much smaller load capacitance.

Matching resistor 34 is located in series with the emitter of cascode transistor 30 and can be used to create a matched termination for coaxial cable 16. Use of matching resistor 34 results in some bandwidth loss and may be excluded from the preamplifier if the disadvantage of the loss of bandwidth outweighs the advantages of having a matched termination for coaxial cable 16.

Referring to FIG. 3, imaging system 10 further includes circuitry enabling a single coaxial cable 16 to act as the coupler between the system box 14 and handle unit 12. Diode coupling network 52, containing diodes 52a and 52b, and external diode 50, enable both transmission pulses and input signals from transducer 18 to be transmitted across the single coaxial cable 16. Transmission pulses reverse bias external diode 50 causing the drain of driver 26 to be clamped by the driver's on-chip drain-to-substrate diode, preventing transmission pulses from passing through the driver's drain. Instead, pulses generated at the system box are transmitted through diode coupling network 52 to transducer 18. Back-to-back diodes 52a and 52b prevent the small input signals created at transducer 18 from passing to the coaxial cable 16, and thus, decouple the preamplifier's input from the coaxial cable 16 and the preamplifier output 40.

FIG. 4 illustrates the circuitry used if the transducer signals are multiplexed. A MOSFET switch 56 is located in series with each transistor driver's drain. By controlling the MOSFET switch's gates, the switches 56 can be selectively placed in an "on" or "off" state, such that only the desired driver outputs will be transmitted to system box 14.

The operation of the ultrasound imaging system to produce a preamplified input signal at the system box 14 works as follows. First, a transmission pulse of a high negative voltage, normally between 50 and 200 volts, is transmitted from the main system box 14 to handle unit 12 through coaxial cable 16. External diode 50 located in series with the drain of driver 26 is reversed biased and the pulse is prevented from passing through the drain of driver 26. The transmit pulse will then be passed, as desired, through the diode coupling network 52 and to the transducer 18. During the transmission of the pulse, the preamplifier input is protected by coupling capacitor 44 and protection diodes 46 and 48 located at the preamplifier's input.

The transmission pulse reaching the transducer 18 produces sound waves which are directed into the patient. Components of these sound waves are reflected from internal organs in the patient's body and are echoed back towards the handle unit 12. The transducer 18 converts the acoustical energy of these reflected sound waves into input signals representing characteristics of the sound waves. Diode coupling network 52 effectively becomes an open circuit to the input signal created by the transducer 18 and the input signal is passed through coupling capacitor 44 to the gate of driver transistor 26.

To bias driver transistor 26, the biasing MOSFET switch 28 is momentarily closed after the transmit pulse ends and before the arrival of the input signal at the driver's gate. By properly timing the activation of the reset on switch 28, a stable DC potential will be placed at the driver gate to provide the necessary biasing for driver transistor 26 to produce a modulated current signal which is transmitted through coaxial cable 16 to system box 14.

If the transducer signals are multiplexed, there will be several transducer inputs, each input being amplified by a separate driver transistor 26. Each driver transistor 26 will have a MOSFET switch 56 located in series with the transistor driver's drain, as shown in FIG. 4. By controlling the gates of switches 56, only the selected transistor driver's outputs will be transmitted to system box 14.

The modulated current signal is then transferred to the cascode transistor's emitter through coaxial cable 16. Properly biased cascode transistor 30 outputs an amplified voltage signal across load resistor 38. The preamplifier output 40 is then processed at the system box 14 to produce ultrasound images.

The split-cascode preamplifier of the present invention 10 has several advantages. By placing the load resistor 38 in the system box 14, the load resistor 38 is not followed by coaxial cable 16 which has a high capacitance. The load resistor 38 can now be selected for high gain because the load resistor 38 is faced with a much smaller load capacitance. Another primary advantage of the split-cascode design is the extremely low power dissipation realized in the transducer handle unit 12 since the drain-to-source voltage of driver transistor 26 can be as little as 1 volt. If the power dissipation in the handle unit 12 is not controlled, the transducer handle unit 12 will burn the patient. However, the noise performance of the MOSFET driver 26 improves with high bias currents. So, the best approach is high bias current with a low voltage drop in the handle unit 12 as achieved by the split-cascode design.

In addition to medical ultrasound systems, other applications requiring a remote sensor that is coupled to a structurally detached system box may also benefit from the present invention.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A medical ultrasound imaging device comprising:
   a) a handle unit including means for converting electrical transmission pulses into output sound waves that are directed towards a patient's body, and sensing means for sensing the reflected sound waves and converting the reflected sound waves into electrical input signals representing characteristics of the reflected sound waves;
   b) a system box including processing means for processing the input signals to produce an ultrasound image;
   c) transmitting means for transmitting the input signals from the handle unit to the system box; and
   d) a split preamplifier for amplifying the input signals including a driver and an associated load means, wherein said driver is located in the handle unit and connected to the input of the transmitting means, and said load means is located in the system box connected to the output of the transmitting means.

2. The imaging device of claim 1 wherein the driver is a transistor and includes switched biasing means.

3. The imaging device of claim 2 wherein the switched biasing means includes a transistor switch for providing a DC biasing voltage to the driver.

4. The imaging device of claim 1 wherein the means for converting electrical transmission pulses into output sound waves is a transducer and the imaging device further includes a diode coupling network for transmitting transmission pulses to the transducer while blocking the input signals from passing through the diode coupling network, and a diode in series with the driver which is reversed biased by the transmission pulse preventing passage of the transmission pulse through the driver.

5. The imaging device of claim 1 wherein the sensing means includes multiple sensors such that each sensor produces an input signal; and wherein a multiplexing means controls the transmission of input signals from the individual sensors to the system box and includes a plurality of drivers with each driver being associated with at least one sensor and a plurality of multiplex switches connected to associated drivers for controlling transmission of input signals to the system box.

6. The imaging device of claim 1 including an AC coupling device for coupling the sensing means to the driver.

7. A remote sensing device including:
   a) a sensor unit including sensing means for sensing a physical variable and means for converting the sensed physical variable into an input signal representing a characteristic of the sensed physical variable;
   b) a system box including processing means for processing input signals to produce an output;
   c) transmitting means for transmitting input signals from the sensor unit to the system box; and
   d) a split preamplifier for amplifying input signals including a driver and an associated load means, wherein said driver is located in the sensor unit and connected to the input of the transmitting means, and said load means is located in the system box connected to the output of the transmitting means.

8. The sensing device of claim 7 wherein the driver is a transistor and includes switched biasing means.

9. The sensing device of claim 8 wherein the switched biasing means includes a transistor switch which provides a DC biasing voltage to the driver.

10. The imaging device of claim 7 wherein the sensing means includes multiple sensors such that each sensor produces an input signal; and wherein a multiplexing means controls the transmission of input signals from the individual sensors to the system box and includes a plurality of drivers with each driver being associated with at least one sensor and a plurality of multiplex switches connected to associated drivers for controlling transmission of input signals to the system box.

11. The sensing device of claim 7 including an AC coupling device for coupling the sensing means to the driver.

12. A medical imaging device using sound waves to produce images used as a diagnostic tool in medicine, comprising:
   a) a handle unit including means for converting electrical transmission pulses into output sound waves that are directed towards a patient's body and sensing means for sensing reflected sound waves and producing electrical input signals representing characteristics of the reflected sound waves;
   b) a system box including processing means for processing the input signals to produce an ultrasound image;
   c) means for transmitting the input signals between the handle unit and the system box; and
   d) a split-cascode preamplifier for amplifying the input signals including:
      1. a drive stage including a common source transistor located in the handle unit and connected to one end of the transmitting means; and
      2. a load stage connected to the opposite end of the transmitting means including a load and a cascode device interposed between the load and the transmitting means.

13. The imaging device of claim 12 wherein the cascode device is a common base transistor.

14. The imaging device of claim 12 including switching means for biasing the common source transistor in the drive stage.

15. The imaging device of claim 12 including an AC coupling device for coupling the transducer to the drive stage of the preamplifier.

16. The imaging device of claim 12 wherein the sensing means includes multiple sensors such that each sensor produces an input signal; and wherein a multiplexing means controls the transmission of input signals from the individual sensors to the system box and includes a plurality of drivers with each driver being associated with at least one sensor and a plurality of multiplex switches connected to associated drivers for controlling transmission of input signals to the system box.

17. A medical ultrasound imaging device comprising:
   a) a handle unit including means for converting electrical transmission pulses into output sound waves that are directed towards a patient's body, and sensing means for sensing the reflected sound waves and converting the reflected sound waves into electrical input signals representing characteristics of the reflected sound waves;
   b) a system box including processing means for processing the input signals to produce and ultrasound image;
   c) transmitting means for transmitting the input signals from the handle unit to the system box; and
   d) a split preamplifier for amplifying the input signals including
      1) a driver and an associated load means, wherein said driver is located in the handle unit and connected to the input of the transmitting means,
      2) a load means located in the system box connected to the output of the transmitting means, and
      3) a cascode device located in the system box and connected between the load means and the transmitting means.

18. The imaging device of claim 17 wherein a matching resistor is interposed between the cascode device and the transmission means for creating a matched termination for the transmission means.

19. A remote sensing device including:
   a) a sensor unit including sensing means for sensing a physical variable and means for converting the sensed physical variable into an input signal representing a characteristic of the senses physical variable;
   b) a system box including processing means for processing input signals to produce an output;

c) transmitting means for transmitting input signals from the sensor unit to the system box; and d) a split preamplifier for amplifying input signals including 1) a driver and an associated load means, wherein said driver is located in the sensor unit and connected to the input of the transmitting means, 2) a load means located in the system box connected to the output of the transmitting means, and 3) a cascode device located in the system box and connected between the load means and the transmitting means.

20. The sensing device of claim 19 wherein a matching resistor is interposed between the cascode device and the transmission means for creating a matched termination for the transmission means.

* * * * *

UNITED STATES PATENT AND TRADEMARK OFFICE
CERTIFICATE OF CORRECTION

PATENT NO. : 5,271,403
DATED : December 21, 1993
INVENTOR(S) : John J. Paulos

It is certified that error appears in the above-indentified patent and that said Letters Patent is hereby corrected as shown below:

```
Column 1, line 16:   delete "the" and insert --then--;
Column 1, line 49:   delete "element" and insert --elements--;
Column 7, line 47:   delete "imaging" and insert --sensing--;
Column 8, line 42:   delete "and" and insert --an--;
Column 8, line 65:   delete "senses" and insert "sensed".
```

Signed and Sealed this

Twenty-third Day of August, 1994

Attest:

BRUCE LEHMAN

Attesting Officer    Commissioner of Patents and Trademarks